(12) United States Patent
Atalar et al.

(10) Patent No.: US 6,284,971 B1
(45) Date of Patent: Sep. 4, 2001

(54) ENHANCED SAFETY COAXIAL CABLES

(75) Inventors: Ergin Atalar, Columbia, MD (US); Ogan Ocali, Santa Clara, CA (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/449,027

(22) Filed: Nov. 24, 1999

Related U.S. Application Data (60) Provisional application No. 60/109,955, filed on Nov. 25, 1998.

(51) Int. Cl.$^7$ .................................................. H01B 7/18
(52) U.S. Cl. ........................ 174/36; 174/102 R; 333/12
(58) Field of Search .................... 174/28, 36, 102 R, 174/106 R; 333/12, 207, 243

(56) References Cited

U.S. PATENT DOCUMENTS

| | | |
|---|---|---|
| 2,322,971 | 6/1943 | Roosenstein . |
| 2,812,502 | 11/1957 | Doherty . |
| 3,601,721 | 8/1971 | Justice . |
| 4,004,257 | 1/1977 | Geissler . |
| 4,052,661 | 10/1977 | Higham et al. . |
| 4,365,109 | 12/1982 | O'Loughlin . |
| 4,620,155 | 10/1986 | Edelstein . |
| 4,649,348 | 3/1987 | Flugan . |
| 4,680,548 | 7/1987 | Edelstein et al. . |
| 4,692,705 | 9/1987 | Hayes . |
| 4,740,752 | 4/1988 | Arakawa et al. . |
| 4,820,987 | 4/1989 | Mens . |
| 4,859,950 | 8/1989 | Keren . |
| 4,887,039 | 12/1989 | Roemer et al. . |
| 4,952,879 | 8/1990 | Van Vaals et al. . |
| 5,543,712 | 8/1996 | Arakawa et al. . |
| 5,621,323 | 4/1997 | Larsen . |

OTHER PUBLICATIONS

C&M Corporation, "Engineering Design Guide", pp. 10 and 11, 1992.*
R. Schetgen, The ARRL Handbook for Radio Amateurs, Seventy–Second, The American Radio Relay League, pp. 19.10–19.17, Newington, CT (1995).

* cited by examiner

Primary Examiner—Chau N. Nguyen
(74) Attorney, Agent, or Firm—Arnold B. Silverman; Eckert Seamans Cherin & Mellott, LLC (57) ABSTRACT

A coaxial cable which may be a magnetic resonance imaging coaxial cable is designed for enhanced safety so as to reduce the risk of excessive heating or burns to a user. The cable has an elongated axially oriented inner conductor and an axially oriented outer shield conductor in spaced relationship with respect thereto with a first dielectric material disposed therebetween. The outer shield conductor has an annular inner shield portion and segmented outer shield portions which are electrically connected to the inner shield portion. In certain preferred embodiments, a second dielectric material having a higher dielectric constant than the first dielectric material is disposed between the inner shield portion and the segmented outer shield portions. In one embodiment, an electrically conductive element extends between the segmented outer shield portions and the inner shield portion and terminates in spaced relationship therewith. In another embodiment, a capacitor may be introduced between the inner shield portion and the segmented outer shield portions.

15 Claims, 4 Drawing Sheets

ENHANCED SAFETY COAXIAL CABLES

This application claims the benefit of U.S. Provisional application Ser. No. 60/109,955 filed Nov. 25, 1998.

BACKGROUND OF THE INVENTION

1. Field of the Invention

The present invention relates to enhanced safety coaxial cables which resist excessive heating and possible burns resulting from undesired induced RF currents on the electrical cables.

2. Description of the Prior Art

The advantageous use of coaxial cables having an inner axially oriented elongated conductor separated from an annular electrically conductive shield by a dielectric material has long been known. Such coaxial cables have been used in magnetic resonance imaging, as well as numerous other uses.

Among the important safety concerns related to magnetic resonance imaging technology are the possible burns and excessive heat due to the induced RF currents on the electrical cables. To reduce the risk of such burns, the users of the MR scanners are instructed to minimize patient contact with cables. Such contact, however, is unavoidable in many cases such as when using ECG cables, surface coils, or intracavity coils.

To minimize burns and induced currents on the cables, some commercial MR coils, such as the magnetic resonance coils of GE Medical Systems, for example, use patient safety modules. See FIG. 1. This design decreases the unbalanced currents on the coaxial cable. In addition to patient safety, this design effects reduction in radiation losses and common mode noise in the coil.

Figure 1:
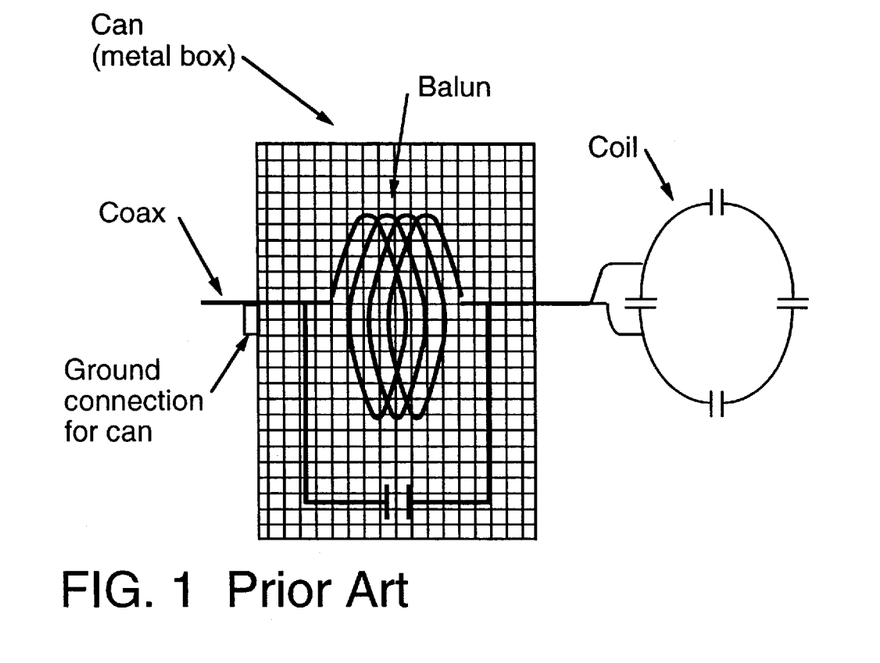
FIG. 1 is an illustration of a prior art magnetic resonance coil.

The operating principle of the prior art design, shown in FIG. 1, is as follows: The signal inside the coaxial cable does not "see" the balun circuit. The balun circuit is effective only with respect to the currents flowing outside the coaxial cable as the unbalanced currents. The capacitor and the number of turns of the coaxial cable is adjusted so that it resonates at the operating frequency. The circuit is encapsulated inside a "can" (or a metal box) with a ground connection at one end so that when an external RF pulse is applied, there will be no current induction in the balun circuit. The resonance circuit will behave as an open circuit for external RF signal and practically eliminates the unbalanced current flowing from cable to the coax. This circuit is an open circuit for the unbalanced current only. The common mode signal (the signal between the inner conductor and the shield of the coaxial cable) will not be affected by the presence of this circuit.

Figure 2:
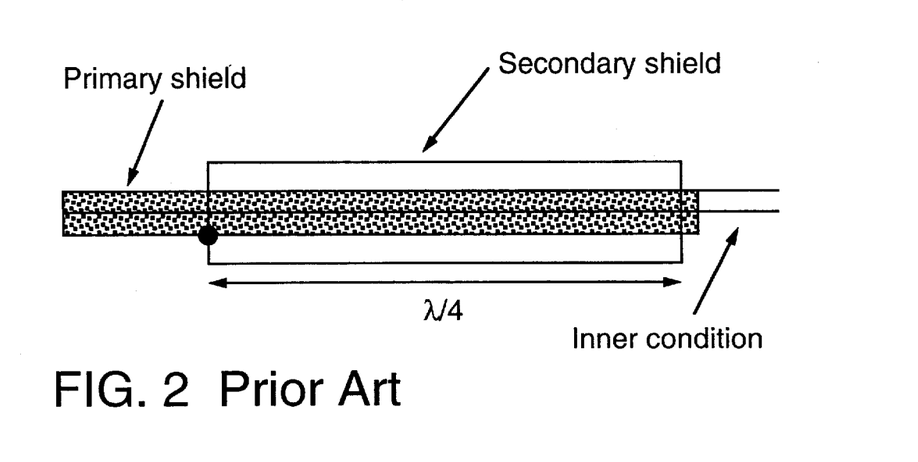
FIG. 2 is a schematic illustration of a prior art balun circuit.

An extension of the above mentioned design is to use other kinds of balun circuits. In the ARRL Handbook for Radio Amateurs, some other balun circuit designs are shown. See R. Schetgen, "The ARRL Handbook for Radio Amateurs," Seventy-Second, The American Radio Relay League, Newington, Conn. (1995). This design is based on the balun (balanced unbalanced transformer) circuit. A typical balun circuit is shown in FIG. 2.

Similar and more serious problems exist for the coils that are inserted inside the body such as endorectal, esophageal, and intravascular RF probes. As these devices are closer to the body, the risk of burning a patient is increased. Also, the wavelength of the RF signal in the body is approximately nine times shorter as compared with the wavelength in the air. As a result, current induction on short cables is possible.

There remains, therefore, a need for an improved coaxial cable which will perform effectively for its intended purpose while resisting undesired excessive heating or burning of a patient or those working with a system as a result of induced RF currents on the electrical cables.

SUMMARY OF THE INVENTION

The present invention provides a new cable design that will reduce the induced currents and hence the risk of excessive heating and burns in uses involving a magnetic resonance imaging scanner. This cable design is useful for increasing the safety of RF probes that are inserted into the body such as endorectal, esophageal, and intravascular RF probes.

The present invention has met the above described need by providing a coaxial cable which may be a magnetic resonance imaging cable having an elongated axially oriented inner conductor, an axially oriented outer shield conductor disposed in spaced surrounding relationship with respect to the inner conductor and a first dielectric material is interposed between the inner conductor and the outer shield conductor. The outer shield conductor is provided with an annular inner shield portion and a segmented inner outer shield portion. Electrically conductive means connect the inner shield portion with the outer shield portion segments. A second dielectric material having a higher dielectric constant than the first dielectric material is interposed between the inner shield portion and the segmented outer shield portions.

Various means for electrically interconnecting the inner shield portion and the segmented outer shield portions, as well as refinements to both the electrically conductive and dielectric portions of the cable are provided.

It is an object of the present invention to provide an improved coaxial cable which is adapted to resist undesired heating of the cable due to induced RF currents.

It is a further object of the present invention to provide a magnetic resonance imaging coaxial cable which has an outer conductor composed of an inner shield portion and a plurality of segmented outer shield portions which are electrically connected to the inner shield portion.

It is a further object of the invention to provide such a system which can be employed with conventional systems using coaxial cables including magnetic resonance imaging systems.

These and other objects of the invention will be more fully understood from the following description of the invention on reference to the illustrations appended hereto.

DESCRIPTION OF THE PREFERRED EMBODIMENTS

As employed herein the term "magnetic resonance imaging" refers to both the use of magnetic resonance apparatus and procedures to generate an image and in spectrographic uses.

The induced current on a electrical cable is determined by the length, orientation of the cable, as well as the amount of applied RF power and the characteristics of the external RF coil that emits the RF power.

When a cable with a length of a half wavelength or longer, the induced currents on the cable might be high depending on the orientation of the cable with respect to the transmitter. On the other hand, when the cable length is smaller than quarter wavelength, the induced currents on the cable will be small regardless of the orientation of the cable.

The best way to increase safety is to use a cable length less than the quarter wavelength. The dielectric constant of the body and the operating frequency determines the wavelength. For example, for a 1.5 T system, the operating frequency for proton is 63.9 MHz. At this frequency, the average dielectric constant of human body is approximately 77. The half wavelength is approximately 20 cm. Therefore, the bare cables inserted into the body that are longer than 20 cm can cause burns depending on their position. On the other hand, the cables with a length of 10 cm or less will have insignificant effect.

In some interventional applications, the minimum cable length is much longer than 20 cm. Therefore, it is advisable to divide the cables in small segments. The present method to divide the cable into small segments from the perspective of external electromagnetic waves, while keeping the coaxial cable intact.

Several embodiments of safe coaxial cable designs of the present invention are shown in FIGS. 3–6. A main objective is to develop a resonant structure embedded inside the cable so that at the operating frequency the structure will behave like an open circuit.

Figure 3:
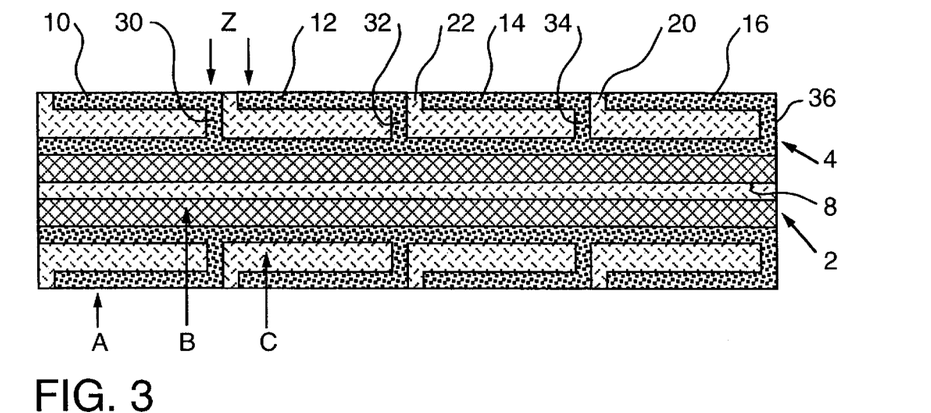
FIG. 3 is a cross-sectional view of one embodiment of coaxial cable of the present invention.

Referring to FIG. 3, there is shown a first embodiment of a coaxial cable A of the present invention. The cable has a generally axially oriented inner conductor 2, an outer shield conductor 4 which is positioned in relative spaced relationship with respect to the inner conductor 2. A first dielectric material B is interposed between the inner conductor 2 and outer shield conductor 4. The outer shield conductor 4 has an annular substantially continuous inner portion 8 and a plurality of axially extending outer shield portions such as 10, 12, 14, 16. The outer shield portions 10, 12, 14, 16 are preferably annular and continuous and are generally aligned with each other having their end portions spaced from each other, such as space 20 between portions 14 and 16, and space 22 between portions 12 and 14, for example. A second dielectric material C is positioned between the inner shield portion 8 and the segmented outer shield portions 10, 12, 14, 16. Dielectric material C has a higher dielectric constant than dielectric material B. The inner dielectric material B preferably is a low loss and low dielectric constant material. The outer dielectric material C is preferably a low loss, high dielectric constant material. This results in impedance Z having a very high value. Each of the outer shield portions 10, 12, 14, 16 is connected to the inner shield portion 8, respectively, by electrically conductive means 30, 32, 34, 36 which, in the form shown, extend generally radially. The axial length of each of the outer shield portions is established such that the impedance Z measured between the gaps, such as 20, 22, is of a very high value. It will be appreciated that while segmenting of the outer shield portions resists undesired induced RF currents that the total cable may be of any desired length.

The structure on the shield of the cable can be thought as a lossy transmission line with a short circuit termination. To increase the impedance Z, the length of the individual outer shield portions 10, 12, 14, 16 should be quarter wavelength where wavelength is calculated based on the dielectric constant of the material "C".

The theory believed to underlie the present invention will be considered. Let $r_0$ and $r_1$, respectively, be the radius of the inner shield portion 8 and outer shield portions 10, 12, 14, 16, respectively. Let the conductivity of the shield be $\sigma_c$ and the dielectric constant and conductivity of the material "C" be $\epsilon_i$ and $\sigma_i$. In this case, the following relationship should be considered.

$$Z = Z_0 \tan h(\gamma \lambda/4) \qquad (1)$$

where:

$Z_0 = \dfrac{R + j\omega L}{G + j\omega C}$ (Characteristic Impedance)

$\gamma = \sqrt{(R + j\omega L)(G + j\omega C)}$ (Wave Propagation Constant)

$\lambda = \dfrac{2\pi}{\omega\sqrt{LC}} = \dfrac{2\pi}{\omega\sqrt{\mu\epsilon_0\epsilon_i}}$ (Wavelength)

$R = \dfrac{1}{2\pi}\left(\dfrac{1}{r_0} + \dfrac{1}{r_1}\right)R_s$ (Distributed Resistance)

$L = \dfrac{\mu}{2\pi}\ln\left(\dfrac{r_1}{r_0}\right)$ (Distributed Inductance)

$C = \dfrac{2\pi\epsilon_0\epsilon_i}{\ln\left(\dfrac{r_1}{r_0}\right)}$ (Distributed Capacitance)

$G = \dfrac{2\pi\sigma_i}{\ln\left(\dfrac{r_1}{r_0}\right)}$ (Distributed Conductance)

$R_s = 1/(\sigma_c \delta)$ (Surface Resistance)

$\delta = \sqrt{\dfrac{1}{\pi f \mu \sigma_c}}$ (Skin Depth)

As can be seen in these equations, the wavelength is independent of the geometry and is the function of the dielectric constant of the material in use. To reduce the total length that of the structure, the dielectric constant has to be maximized.

EXAMPLE I

In order to provide further insight into the invention, an example will be considered.

To generate a sample design, it is assumed that the shield is made of copper and the dielectric material is tetrafluoroethylene which is offered under the trade designation Teflon. Copper has a conductivity of $5.8\times10^7$ ohm$^{-1}$ m$^{-1}$ and Teflon has a dielectric constant of 2.0 and conductivity of $1\times10^{-16}$ ohm$^{-1}$ m$^{-1}$ (data was obtained from the web page of Dupont: <http://www.dupont.com/copr/markets/aerospace/products/240831b.html>). Assume that $r_1$ and $r_0$ are 1 mm and 0.5 mm, respectively. In this case, the length of the structure ($\lambda/4$) is calculated as 83 cm. For this structure, $R_s=2.088\times10^{-3}$ ohm, R=1.00 ohm/m, $L=1.39\times10^7$ H/m, $C=1.61\times10^{-10}$ F/m, $G=9.06\times10^{-16}$ ohm$^{-1}$/m. Therefore, $Z_0=29.4-0.263j$ ohm and $\lambda=0.017+1.90j$ m$^{-1}$. The "j" is the complex number % −1. Given these values, impedance Z can be calculated as 2092−28j ohm. As can be seen, although the Z value is very reasonable, the length of the structure (83 cm) is much longer than needed. Assume that we use an imaginary dielectric material with a very high dielectric constant of 80. In this case, C becomes $6.42 \times 10^{-9}$ F/m and the length of the structure becomes 13 cm, which is very reasonable. In this case, ZO=4.64−0.04151 ohm, and $\lambda$=0.1073+12.00j, and overall Z becomes 331−4.4j ohm.

Figure 4:
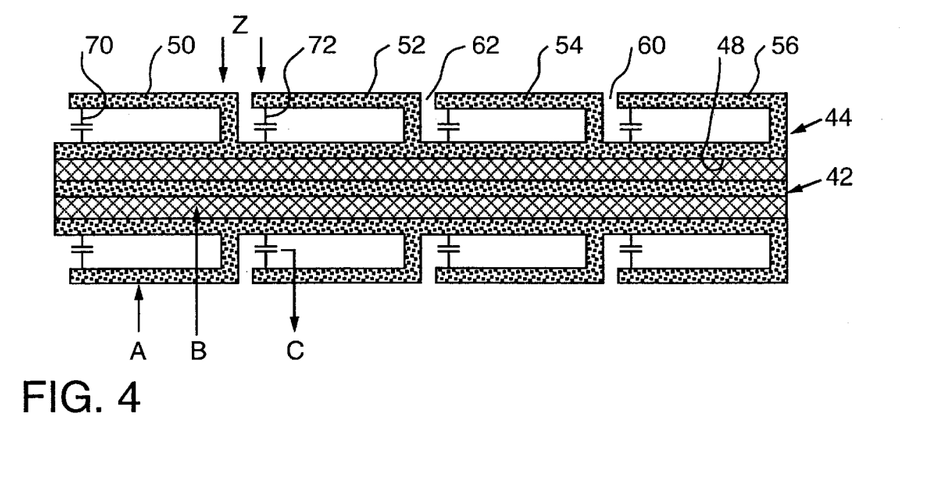
FIG. 4 is a cross-sectional view of another embodiment of the coaxial cable of the present invention employing capacitors.

The coaxial cable of FIG. 4 has an axial cable 42 disposed generally centrally and an outer shield conductor 44 which contains an annular inner conductive portion 48 and a plurality of segmented outer shield portions 50, 52, 54, 56 with gaps therebetween, such as 60, 62, for example. The capacitors, such as 70, 72, for example, may be a plurality of capacitors within a given outer shield portion 50 or an annular continuous one, such as a feed trough capacitor, or any combination which will provide the desired capacitance. Between the outer shield portions 50, 52, for example, are capacitors 70, 72, respectively, with the value of the capacitors 70, 72 and the length of the segment being selected so as to create a very high value for impedance "Z."

In the embodiment shown in FIG. 4, the value of the capacitor is properly selected and the length of each of the segments is tuned to effect a match so that the impedance Z has the maximum possible value.

For this case, the impedance Z can be calculated as:

$$Z = 1/\text{Re}\left\{\frac{1}{Z_0 \tanh(\gamma l)}\right\} \quad (2)$$

and the value of the capacitor, $C_p$, that is necessary for this design to work can be calculated as:

$$C = \frac{1}{\omega}\text{Im}\left\{\frac{1}{Z_0 \tanh(\gamma l)}\right\} \quad (3)$$

where, Re{.} and Im{.} give the real and imaginary part of its operant.

Assume an example design with the length of the structure length, l=5 cm; $r_1$, and $r_2$ are 1 mm and 0.5 mm, respectively; and copper shield with Teflon insulator; the operating frequency is 64 MHz. For this design, Z can be calculated as 39.0 ohm. The capacitance value that is employed in this design to work is $C_p$=3.5 nF.

Figure 5:
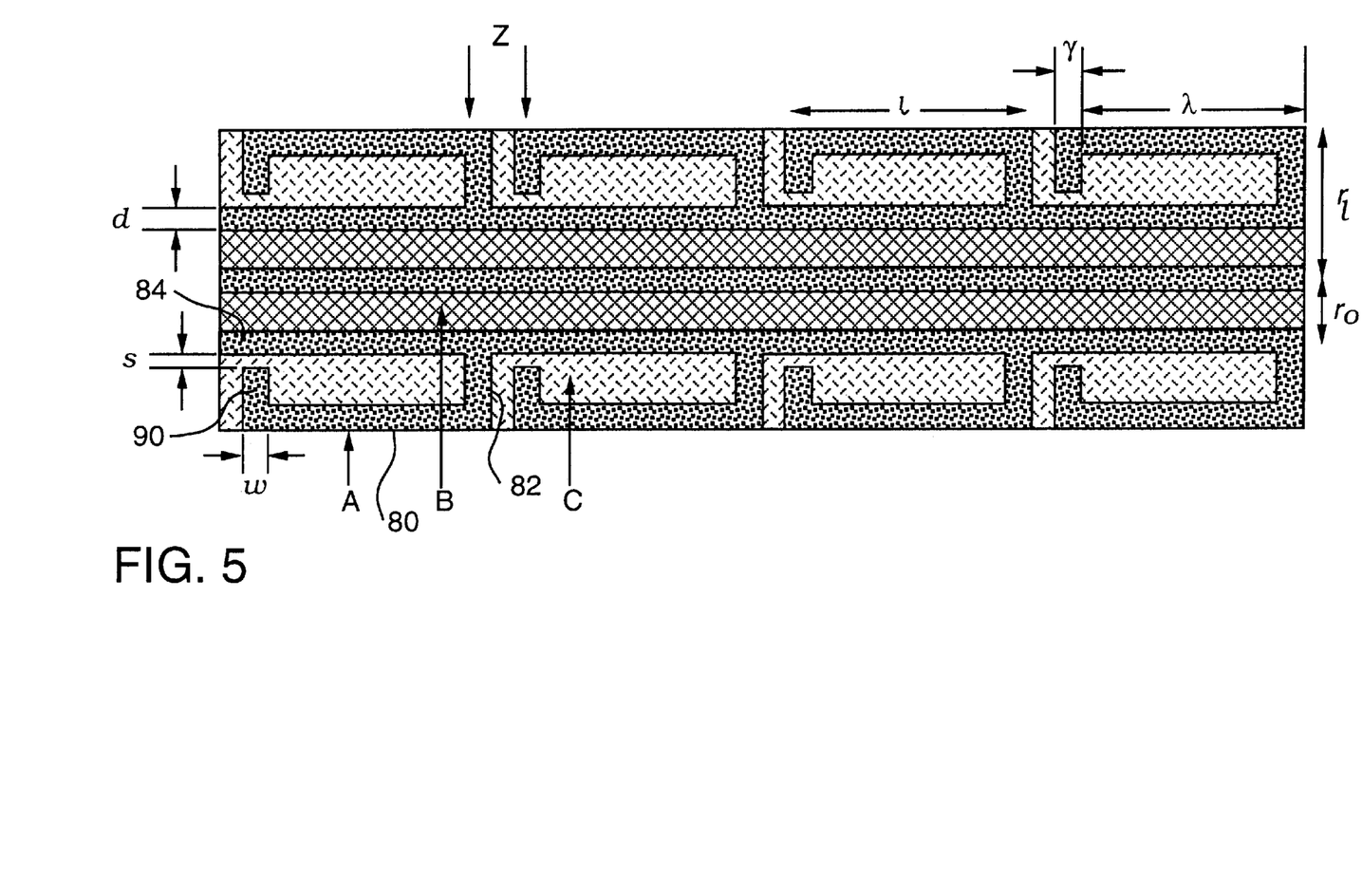
FIG. 5 is a cross-sectional view of a further embodiment of the coaxial cable of the present invention showing both dielectric material and spacing of conductive elements employed in the outer shield conductor.

The embodiment shown in FIG. 5 is similar to the design in FIG. 4 with a difference that the capacitors were built with a structural change. In this embodiment, high dielectric constant material is employed only in the regions where the outer shield portions and the inner shield portion are close to each other as at "s." The desired high impedance value can be obtained in this manner even with the materials with dielectric constants of as low as 2. The values of l, w, s, $r_1$, and $r_0$ (see FIG. 5) should be selected so the impedance Z has a very high value.

In the embodiment of FIG. 5, the segmented inner shield portions, m such as 80, have not only electrically conductive means 82 connecting the outer shield portions with the inner shield portion 84, but also have radially inwardly projecting elements 90 which are electrically conductive and have a width w and terminate in a free end spaced a distance "s" from the outer surface of inner shield portion 84.

The following analysis gives a better understanding how one may select the parameters of the design to maximize the value of Z.

One may analyze the embodiment shown in FIG. 5 as two transmission lines connected to in a cascade form. Symbols "$\lambda$" and "$\gamma$" where "$\lambda$" corresponds to the part that has a wide separation between the two shields and "$\gamma$" corresponds to the part that has a narrow separation between them. In this case, we can reformulate the equations as follows:

$$R_\lambda = \frac{1}{2\pi}\left(\frac{1}{r_0} + \frac{1}{r_1}\right)R_s, \quad R_\gamma = \frac{1}{2\pi}\left(\frac{1}{r_0} + \frac{1}{r_0+s}\right)R_s \quad (4)$$

$$L_\lambda = \frac{\mu}{2\pi}\ln\left(\frac{r_1}{r_0}\right), \quad L_\gamma = \frac{\mu}{2\pi}\ln\left(\frac{r_0+s}{r_0}\right) \quad (5)$$

$$C_\lambda = \frac{2\pi\varepsilon_0\varepsilon_i}{\ln\left(\frac{r_1}{r_0}\right)} \quad C_\gamma = \frac{2\pi\varepsilon_0\varepsilon_i}{\ln\left(\frac{r_0+s}{r_0}\right)} \quad (6)$$

$$G_\lambda = \frac{2\pi\sigma_i}{\ln\left(\frac{r_1}{r_0}\right)} \quad G_\gamma = \frac{2\pi\sigma_i}{\ln\left(\frac{r_0+s}{r_0}\right)} \quad (7)$$

$$Z_{0\lambda} = \frac{R_l + j\omega L_l}{G_l + j\omega G_l} \quad Z_{0\gamma} = \frac{R_c + j\omega L_c}{G_c + j\omega G_c} \quad (8)$$

$$\gamma_\lambda = \sqrt{(R_\lambda + j\omega L_\lambda)(G_\lambda + j\omega C_\lambda)} \quad \gamma_\gamma = \sqrt{(R_\gamma + j\omega L_\gamma)(G_\gamma + j\omega C_\gamma)} \quad (9)$$

$$Z = Z_{0\gamma}\tanh\left(w\gamma_\gamma + \tanh^{-1}\left(\frac{Z_{0\lambda}}{Z_{0\gamma}}\tanh((l-w)\gamma_\lambda)\right)\right) \quad (10)$$

The above expression is rather complex, and difficult to optimize. As a first order approximation, we assumed that both R and G are zero. The derivative of Z with respect to "w" and results in the following approximate solution for the value of w that maximizes Z.

$$w = \frac{l}{2} - \frac{1}{2\omega\sqrt{\mu\varepsilon_0\varepsilon_i}}$$

$$\cos^{-1}\left[\frac{\ln\left(\frac{r_1}{r_0}\right)/\ln\left(\frac{r_0+s}{r_0}\right)+1}{\ln\left(\frac{r_1}{r_0}\right)/\ln\left(\frac{r_0+s}{r_0}\right)-1}\cos\left(\omega l\sqrt{\mu\varepsilon_0\varepsilon_i}\right)\right] \quad (11)$$

We experimentally found out that the optimum value of "s" tends to be that which increases "w" to a value close to length (lower case "L") ½. In other words, the best "s" value makes the second term of the above equation small, the term in the inverse cosine function be unity.

$$s_{critical} = r_1\left[1 - \left(\frac{r_0}{r_1}\right)^{\frac{1-\cos(\omega l\sqrt{\mu\varepsilon_0\varepsilon_i})}{1+\cos(\omega l\sqrt{\mu\varepsilon_0\varepsilon_i})}}\right] \quad (12)$$

For a small values of length (lower case "L") l, the above equation can further be simplified as:

$$s_{critical} \approx r_1\omega^2 l^2 \mu\varepsilon_0\varepsilon_i \ln\left(\frac{r_0}{r_1}\right) \quad (13)$$

EXAMPLE II

Assume the following case: length l=5 cm, $r_0$=1 mm, $r_1$=0.5 mm, and assuming copper is used as the conductor and Teflon is the insulator. The value w is calculated as 2.21 cm, and s is calculated as 1.52 µm. In these conditions, the overall impedance Z is calculated as 50.6−1.4j ohm.

Figure 6:
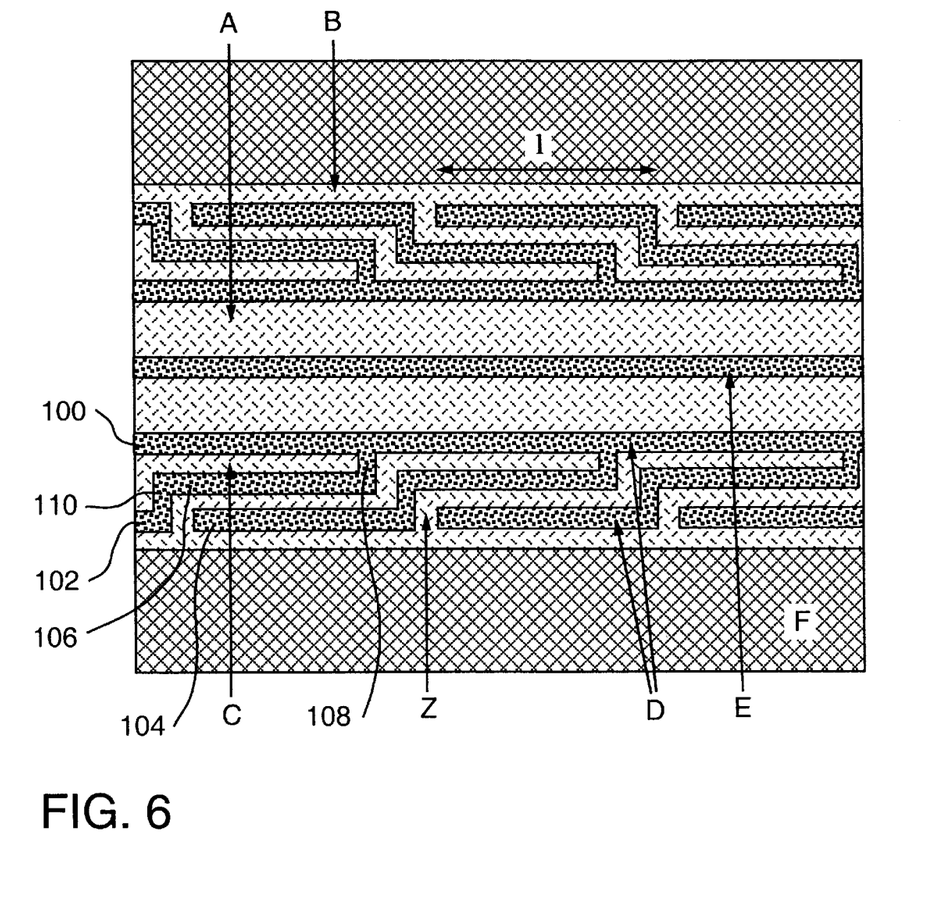
FIG. 6 is a cross-sectional illustration of a coaxial cable of the present invention having modified form of segmented outer shield portions.

A multi-layer safe-coaxial cable design is shown in FIG. 6. This design has the same basic philosophy as the design shown in FIG. 3. As it was discussed, the basic design requires a very high dielectric constant material or long structure. In FIG. 6, the embodiment multi-layer long structures are shown. While the length of conductor exposed to the external field is length "1", the length of the structure is "21". The formulation of the design is the same as given in the basic design, except length "1" in the equations has to be replaced by "21."

As shown in FIG. 6, adjacent to the inner conductor E is a low loss, low dielectric constant material A, which may be Teflon. Low loss, low dielectric constant material A is therefore interposed between the inner conductor E and the shield D. A low loss, high dielectric constant material C is interposed between the inner shield portion 100 and the outer shield portion 102. This material may be titanium dioxide, for example. The outer conductive portions 102, 104 have a length, and are interconnected with the inner shield portion 100 by an elongated conductive member 106 and a pair of generally radially oriented portion 108, 110 to create a step-like arrangement. The coaxial cable is insulated with a low dielectric constant material B. The entire coaxial cable is, in the form shown, disposed within a human body portion F or other environment. In order to maximize the impedance Z, the length 1 is chosen such that the impedance is maximized. This length is generally ⅛ wavelength in the dielectric material C. It is preferred that length "1" be less than the quarter wavelength of the medium F.

The present invention provides sample designs for safe coaxial cable designs. The safety of these cables can further be increased by insulating the cable with a resinous plastic material. The calculations herein will not be effected by the insulation, because all the calculations shown here are related to the electrical properties of the inside of the structure. The effect of insulation, however, will be significant for the external magnetic field. From the perspective of the external field, the apparent wavelength on the cable increases with the insulation. Therefore, the requirement for dividing the cable to very short outer shield portions can be relaxed to permit use of longer portions.

This invention can be used in other cable types such as single conductor cables, multi conductor cables with and without a shield. If desired, the inner conductor can be formed from a plurality of conductor elements in contact with each other or spaced from each other. Reference herein to "an elongated axially oriented inner conductor" will embrace such a construction. The applications are not limited to the cables of the probes that will be inserted into the body. Any cable that has possibility of getting close to the patient will benefit from this design because of the increased safety.

The invention is not limited to 64 MHz (proton resonance frequency at 1.5 Tesla). Using the generic formulation given herein, one may design safe-coaxial cables at practically all operating frequencies. The examples employed 64 MHz in our examples because it is the most commonly used frequency. Other common frequencies include 200 MHz, 170 MHz, 42 MHz, 21 MHz, 6.4 MHz.

The safe-coax cable design may have application other than magnetic resonance imaging. It can be used in any circuit that requires low unbalanced currents at a specific operating frequency. For example, if the field pattern of an antenna is affected by the presence of a nearby cable this cable can be provided with the safe-coax structures described earlier.

In this disclosure, we have presented a novel coaxial cable design method. The invention places resonance circuits/structures along the length of a coaxial cable with short intervals. In this way, an external field could not induce current on the cable.

Whereas particular embodiments of the invention have been described above for purposes of illustration it will be appreciated by those skilled in the art that numerous variations of the details may be made without departing from the invention as described in the appended claims.

What is claimed is:

1. An induced RF current inhibiting coaxial cable comprising
    an induced RF current inhibiting an elongated axially oriented inner conductor,
    an axially oriented outer shield conductor disposed in spaced surrounding relationship with respect to said inner conductor,
    a first dielectric material interposed between said inner conductor and said outer shield conductor,
    said outer shield conductor having an annular inner shield portion and segmented outer shield portions,
    electrically conductive means electrically connecting said inner shield portion to said segmented outer shield portions,
    a second dielectric material interposed between said segmented outer shield portions and said inner shield portion, and
    said second dielectric material having a higher dielectric constant than said first dielectric material.
2. The coaxial cable of claim 1 including
    said coaxial cable being a magnetic resonance coaxial cable.
3. The coaxial cable of claim 2 including
    said coaxial cable being the coaxial cable part of a magnetic resonance imaging intracavity coil.
4. The coaxial cable of claim 2 including
    said coaxial cable being the coaxial cable part of a magnetic resonance imaging surface coil.
5. The coaxial cable of claim 2 including
    said segmented outer shield portions being annular.
6. The coaxial cable of claim 1 including
    said segmented outer shield portions being annular.
7. The coaxial cable of claim 6 including
    said electrically conductive means being generally radially oriented.
8. The coaxial cable of claim 1 including
    capacitor means interposed between said segmented outer shield portions and said inner shield portion.
9. The coaxial cable of claim 1 including
    said electrically conductive means including an annular electrically conductive portion and a pair of radial electrical connecting portions with one said radial connecting portion being electrically connected to a said segmented outer shield portion and another being electrically connected to a said inner shield portion.
10. The coaxial cable of claim 9 including
    said outer shield portions having an axial length of less than 10 cm.
11. The coaxial cable of claim 10 including
    said electrically conductive means having a generally step-like configuration.
12. The coaxial cable of claim 1 including
    third dielectric means covering the exterior of said outer shield conductor.

13. A coaxial cable comprising an elongated axially oriented inner conductor, an axially oriented outer shield conductor disposed in spaced surrounding relationship with respect to said inner conductor, a first dielectric material interposed between said inner conductor and said outer shield conductor, said outer shield conductor having an annular inner shield portion and segmented outer shield portions, electrically conductive means electrically connecting said inner shield portion to said segmented out shield portions, a second dielectric material interposed between said segmented outer shield portions and said inner shield portion, said coaxial cable being a magnetic resonance coaxial cable, and generally inwardly projecting portions extending from said segmented outer shield portions toward said inner shield portion and terminating in spaced relationship with respect to said inner shield portion.

14. The coaxial cable of claim 13 including said segmented outer shield portions being in generally aligned spaced relationship with respect to each other.

15. The coaxial cable of claim 13 including said coaxial cable is disposed at least partially within a magnetic resonance imaging scanner.

* * * * *

UNITED STATES PATENT AND TRADEMARK OFFICE
CERTIFICATE OF CORRECTION

PATENT NO. : 6,284,971 B1  Page 1 of 1
DATED : September 4, 2001
INVENTOR(S) : Ergin Atalar et al.

It is certified that error appears in the above-identified patent and that said Letters Patent is hereby corrected as shown below:

<u>Column 4,</u>
First formula, line 1, "Z=$Z_0$ tan h(" should read -- Z=$Z_0$ tanh( --.

Signed and Sealed this

Eleventh Day of June, 2002

Attest:

Attesting Officer

JAMES E. ROGAN
*Director of the United States Patent and Trademark Office*